United States Patent [19] [11] 4,022,456
Hooper et al. [45] May 10, 1977

[54] METHOD AND APPARATUS FOR FOLDING AND CUTTING AN INTERCONNECTED WEB OF DISPOSABLE DIAPERS OR THE LIKE HAVING STRETCHED ELASTIC LEG BANDS SECURED THERETO

[75] Inventors: Leonard C. Hooper, Cincinnati; Gerald M. Weber, Loveland, both of Ohio

[73] Assignee: The Procter & Gamble Company, Cincinnati, Ohio

[22] Filed: July 11, 1975

[21] Appl. No.: 595,477

[52] U.S. Cl. ............................................. 270/65
[51] Int. Cl.² .................................... B65H 45/16
[58] Field of Search ............. 270/65, 61 R, 76–77, 270/21, 69; 156/467; 93/84 R; 223/37; 83/452, 925 CC

[56] References Cited
UNITED STATES PATENTS

| | | | |
|---|---|---|---|
| 3,483,780 | 12/1969 | Hudson | 83/81 |
| 3,537,461 | 11/1970 | Imbert | 270/76 |
| 3,557,156 | 1/1971 | Enneper | 156/383 |
| R28,139 | 8/1974 | Gore | 156/467 |

OTHER PUBLICATIONS

B516,609, Feb. 1976, Nystrand, 270/62.

*Primary Examiner*—Edgar S. Burr
*Assistant Examiner*—A. Heinz
*Attorney, Agent, or Firm*—E. Kelly Linman; Fredrick H. Braun; John V. Gorman

[57] ABSTRACT

An interconnected web of disposable diapers containing a pair of continuous, stretched strands of elastic aligned generally parallel to the direction of web travel, is folded along its length from a substantially flat condition to produce a C-shaped, transverse cross-section by means of a conventional board and guide folder. The C-folded web is maintained under tension during the longitudinal folding operation to keep the continuous elastic strands in a stretched condition, and the web is cut transverse to the direction of web travel without releasing the tension in either the individual diapers cut from the web or in the advancing web. Means are provided for transversely folding the individual diapers cut from the web about their midpoints while maintaining the elastic strands associated therewith in a stretched condition and the diaper under positive control. Because the advancing web of interconnected diapers is maintained under positive control at all times, the individual diapers severed from the web are cut in register with respect to one another. This is of critical importance in situations where the web of interconnected disposable diapers is comprised of a plurality of discrete, interconnected diaper segments rather than a continuous web of disposable diaper material having a uniform cross-section throughout its length.

22 Claims, 24 Drawing Figures

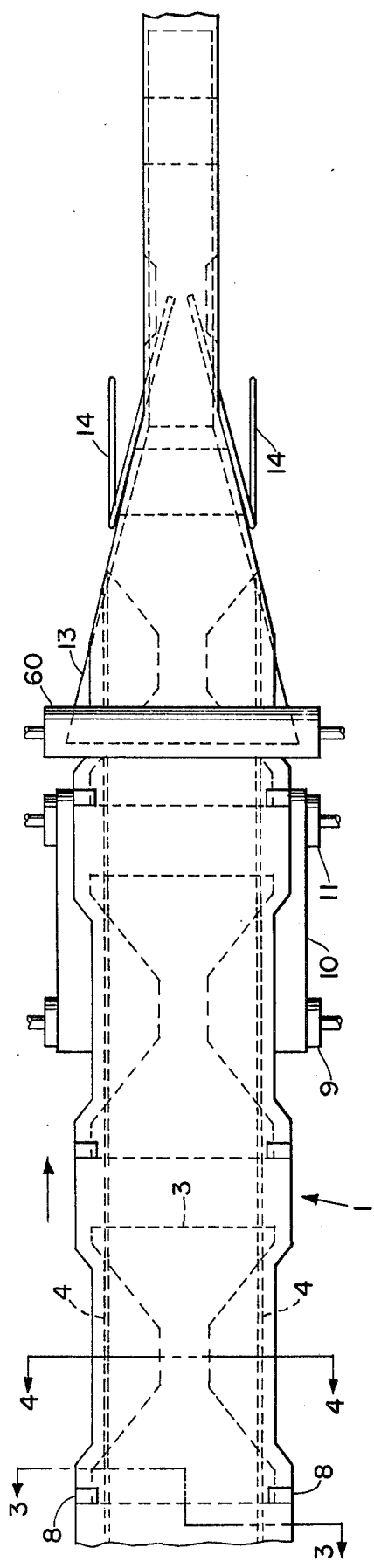
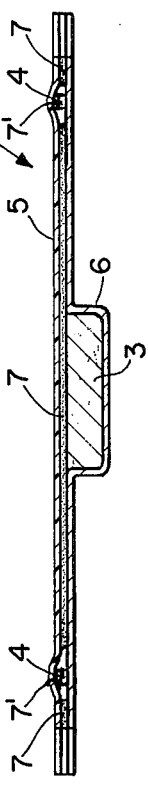
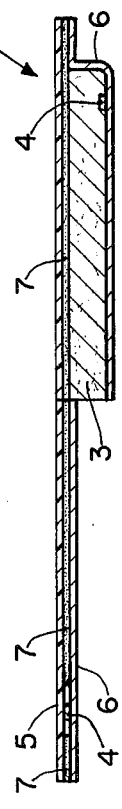
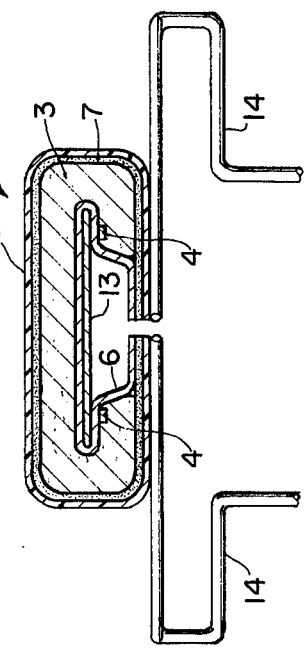
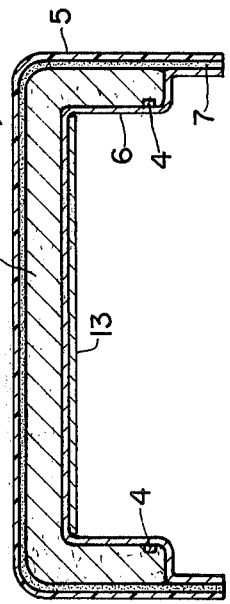

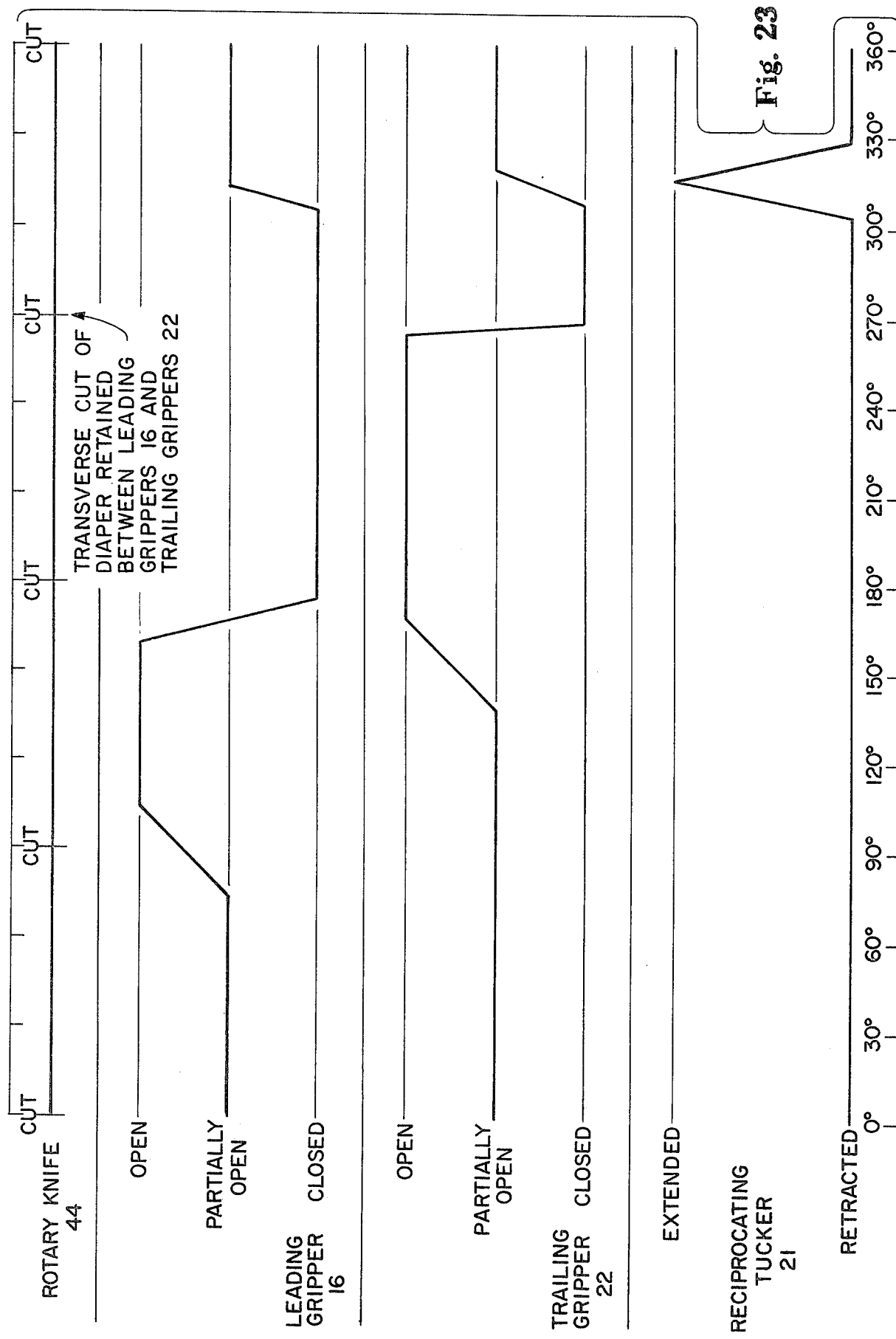

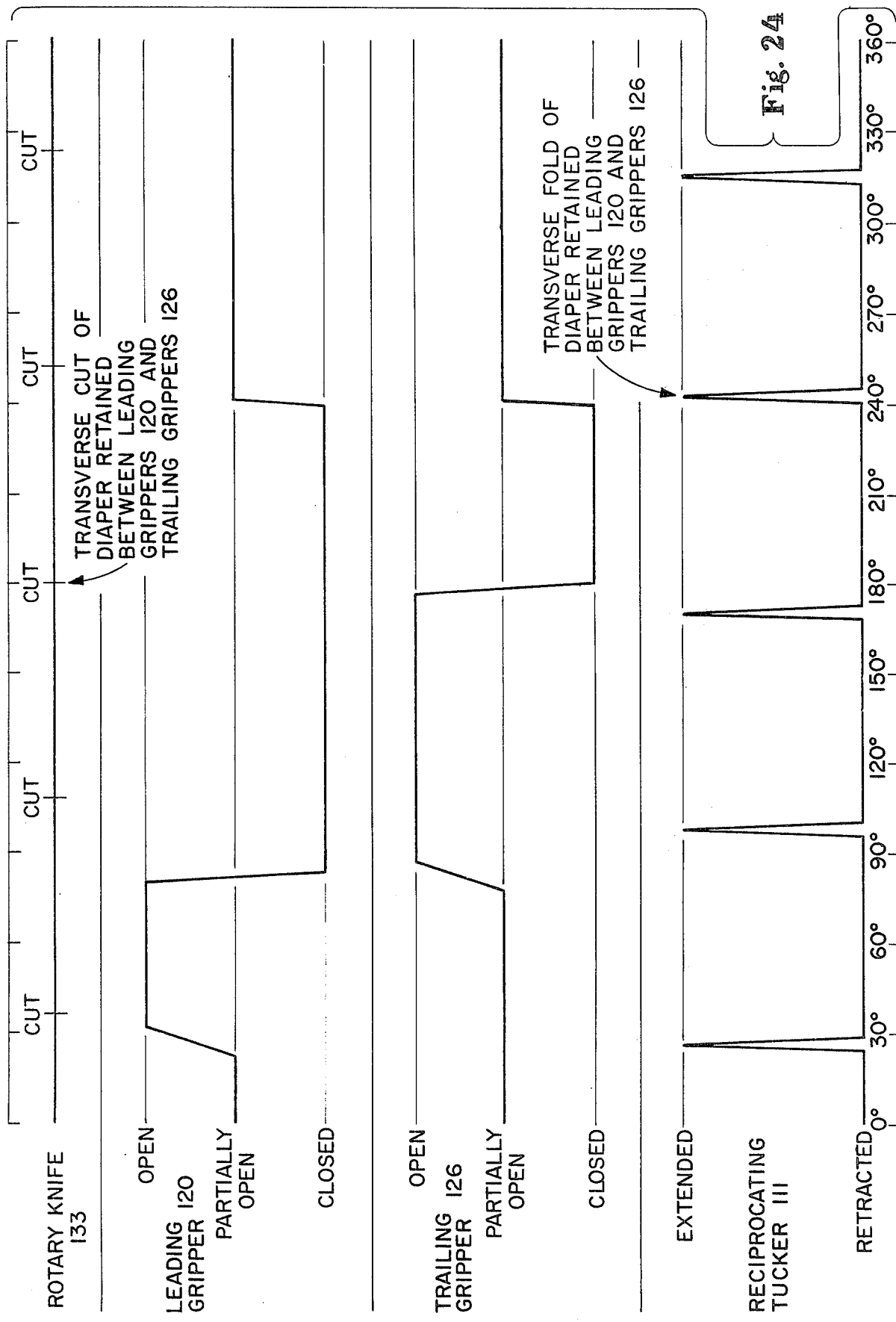

METHOD AND APPARATUS FOR FOLDING AND CUTTING AN INTERCONNECTED WEB OF DISPOSABLE DIAPERS OR THE LIKE HAVING STRETCHED ELASTIC LEG BANDS SECURED THERETO

BACKGROUND OF THE INVENTION

Method and apparatus for longitudinally folding a continuous web of disposable diaper material and for transversely cutting the web into individual diaper segments are well known in the art. For example, U.S. Pat. No. 3,557,156 which issued to Enneper et al. on Jan. 19, 1971 discloses an apparatus for feeding a continuous web of stretchable diaper material and for performing successive operations thereupon. It should be noted, however, that the term "elastic", as utilized in the patent to Enneper et al., refers to the inherent tendency of the web to stretch to various degrees when subjected to tension rather than to the presence of stretched strands of elastic as disclosed in U.S. Pat. No. 3,860,003 which issued to Buell on Jan. 14, 1975 and which is hereby incorporated herein by reference. The patent to Enneper et al. discloses a plurality of sectional drives which serve to advance a folded diaper web through the various sections of a processing machine at a predetermined linear speed as well as to control the tension in the web at the respective sections. The desired tension in the web is obtained by adjusting the speed of one sectional drive relative to that of an adjacent sectional drive.

U.S. Pat. Re. 28,139 which issued to Gore on Aug. 27, 1974 likewise discloses prior art apparatus for forming conventional disposable diapers, i.e., disposable diapers which do not have stretched strands of elastic aligned generally parallel to the direction of web travel secured thereto. The patent to Gore discloses apparatus for forming a continuous web of disposable diapers, folding the web into a predetermined cross-sectional configuration, separating the web into individual diapers, and transversely folding the diapers prior to packaging.

U.S. Pat. No. 3,483,780 which issued to Hudson on Dec. 16, 1969 discloses prior art apparatus for pinch cutting a plurality of abrasive-containing filaments. Feed rollers are provided at the entrance into the cutter to insure movement of the mterials to be cut at a constant rate of speed. Grippers are provided for feeding the material to be cut to the cutting zone and for carrying away the cut material. The grippers prevent the ends of the cut material from flying out in various diverse directions.

None of the systems disclosed in the aforementioned patents would, however, be suitable for performing a series of operations under positive control and in accurate register on a continuous web of discrete articles, said web containing continuous strands of stretched elastic adhered thereto at spaced locations along its length, and for maintaining the discrete articles under positive control without loss of register after severance of said articles from said web.

OBJECTS OF THE INVENTION

Accordingly, it is an object of the present invention to provide method and apparatus for longitudinally C-folding an interconnected web of discrete disposable diapers, said web containing a pair of continuous, stretched strands of elastic aligned generally parallel to the direction of web travel, for transversely cutting said diapers from said web in register with one another while maintaining the elastic strands associated therewith in a stretched condition, and for transversely folding the individual C-folded diapers cut from said web about their midpoints prior to packaging.

It is another object of the present invention to maintain both the interconnected web and the individual diapers cut therefrom under positive control throughout the longitudinal C-folding, transverse cutting, and transverse folding operations.

It is another object of the present invention to provide method and apparatus for transversely cutting an elasticized web containing a plurality of discrete disposable diaper segments in such a manner that each transverse cut is made in accurate register between adjacent diaper segments.

It is still a further object of the present invention to provide method and apparatus for transversely folding disposable diapers having stretched strands of elastic secured thereto about their midpoints to produce a folded article of uniform size and appearance.

SUMMARY OF THE INVENTION

The problem of longitudinally C-folding, transversely cutting and transversely folding a web of interconnected disposable diapers of the type generally disclosed in U.S. Pat. No. 3,860,003 which issued to Buell on Jan. 14, 1975 and which has been incorporated herein by reference is complicated by the presence of continuous, stretched strands of elastic aligned generally parallel to the direction of web travel and secured at spaced locations outboard of and adjacent to the crotch area of each absorbent pad segment. The continuous elastic strands are preferably positioned intermediate a web of topsheet material and a web of moisture-impervious backsheet material. The stretched elastic strands tend to pucker the web when tension on the web is released, thereby posing a difficult problem to longitudinal C-folding, transverse cutting and transverse folding operations, primarily in the form of poor web control and poor registration from one diaper to the next.

Accordingly, in a preferred embodiment of the present invention, the C-folded diaper web is maintained under tension by means of cooperation between a vacuum hold-down belt and a plurality of cam actuated grippers mounted on the periphery of a rotating drum. The first or leading pair of cam-actuated grippers which secure the leading edge of the web serve to advance the web a predetermined distance in order to place each diaper contained in the web in register with a rotary flex knife utilized to transversely cut individual diaper segments from the web. Just before the transverse cut is made, an additional or trailing pair of cam-actuated grippers located near the trailing edge of the disposable diaper segment being severed are closed to maintain the individual diaper under tension, thereby preventing puckering and loss of registration during the transverse folding operation. At approximately the same time, another pair of cam-actuated leading grippers located just ahead of the rotary flex knife are closed in order to maintain the advancing web under tension upon completion of the cut. The individual diapers cut from the web are preferably maintained under tension until the approximate instant they are introduced at their midpoints between a pair of folding belts by means of a reciprocating tucker mechanism located on the periphery of the drum between each set of leading and trailing grippers.

In a most preferred embodiment of the present invention, the folding belts which are located at the point of discharge from the rotary drum are oscillated in synchronization with the movement of each diaper on the surface of the drum to increase the dwell tie available for inserting the midpoint of each diaper structure into the nip between the belts. Matching the peripheral velocity of the drum and the peripheral velocity of the nip between the folding belts for a brief interval in this manner permits more reliable and higher speed operation of the entire system.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings in which:

FIG. 2 is a simplified view of the disposable diaper web illustrated in FIG. 1 taken along view line 2—2 of FIG. 1, illustrating the outline of the absorbent pad and the continuous, stretched elastic strands contained in the web;

FIG. 3 is an enlarged, simplified, cross-sectional view taken along section line 3—3 of FIG. 2, illustrating a preferred relationship between the backsheet, the topsheet, the absorbent pad, and the stretched strands of elastic;

FIG. 4 is an enlarged, simplified, cross-sectional view taken along section line 4—4 of FIG. 2, illustrating a preferred relationship between the backsheet, the topsheet, the absorbent pad and the stretched strands of elastic in an area adjacent the recessed crotch portion of the absorbent pad;

FIG. 5 is an enlarged, simplified cross-sectional view taken along section line 5—5 in FIG. 1, illustrating the tendency of the outermost edges of the disposable diapers to drape about the board folder located at the infeed to the rotary drum;

FIG. 6 is an enlarged, simplified cross-sectional view taken along section line 6—6 of FIG. 1, illustrating the tendency of the web guides to cause the outermost portions of the diapers to wrap themselves about the board folder located at the infeed to the rotary drum;

FIG. 23 is a timing chart illustrating a preferred operational relationship between a leading and trailing pair of grippers, the tucking mechanism associated with said grippers, and the rotary knife utilized on the rotary drum system illustrated in FIG. 1; and FIG. 24 is a timing chart illustrating a preferred operational relationship between a leading and trailing pair of grippers, the tucking mechanism and the rotary knife utilized on the chain system illustrated in FIG. 16.

DETAILED DESCRIPTION OF THE INVENTION

Figure 1:
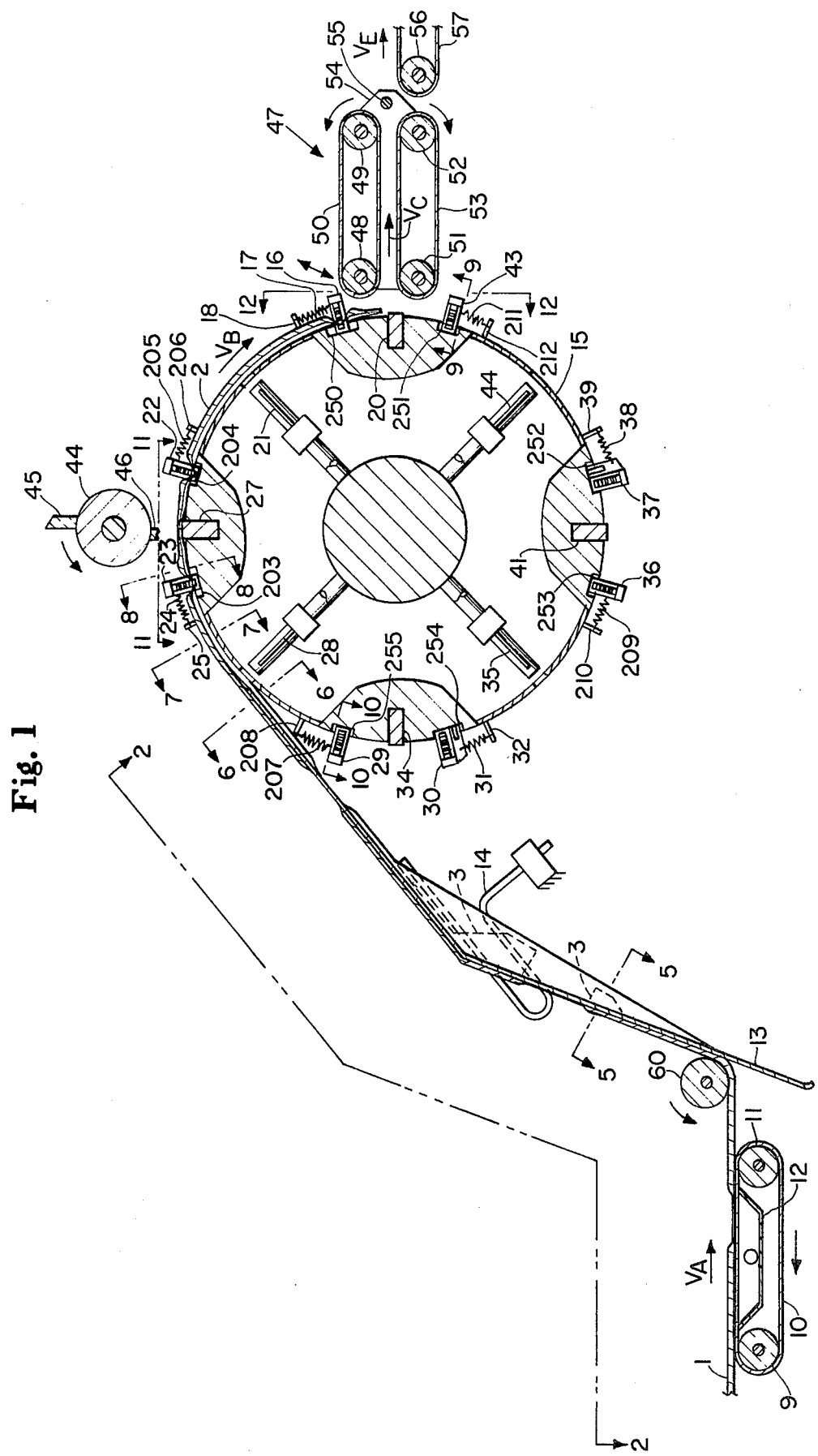
FIG. 1 is a sectional side elevation view showing a web of interconnected disposable diapers of the type generally disclosed in the forementioned patent to Buell being folded from a flat condition into a C-shaped, transverse cross-section prior to feeding the web onto the periphery of a rotating drum having a plurality of gripping elements mounted at spaced locations about its periphery, said view being taken in a plane passing through the centerline of said web and illustrating the condition of the web at the instant an individual diaper is being cut from the web.

Referring to FIGS. 1 and 2, there is shown a continuous web 1 comprised of a plurality of interconnected disposable diapers 2, each diaper being comprised of an absorbent pad element 3, a pair of continuous, stretched elastic strands 4 secured to the web at spaced locations intermediate the recessed portions of the absorbent pad, said absorbent pad and said stretched elastic strands being located intermediate a moisture-impervious backsheet 5 (FIG. 3) and a moisture-pervious topsheet 6 (FIG. 3). The elastic strands 4 preferably have a length sufficient to interconnect the opposing end portions of the hourglass-shaped absorbent pad elements 3. A pair of pressure-sensitive adhesive tape fasteners 8 is preferably secured to the waistband of each diaper for securing the diaper in an operative position about the wearer's waist. Although the web 1 is shown under tension in FIGS. 1 and 2, it should be noted that the stretched elastic strands 4 will tend to pucker the web when tension on the web is released.

U.S. Pat. No. 3,860,003 which issued to Buell on Jan. 14, 1975 and which has been incorporated herein by reference discloses a number of disposable diaper embodiments employing elastically contractible, flexible side portions to which the method and apparatus of the present invention are particularly well suited. It will be readily apparent to those skilled in the art, however, that although the following description of the present invention is in connection with longitudinally folding, transversely cutting and transversely folding a continuous web of interconnected disposable diapers having stretched strands of elastic secured thereto, the present invention may be practiced with equal facility on any continuous web comprised of elastically contractible articles, each article requiring one or more operations to be performed in register thereupon. While mechanical gripping elements are illustrated and described in connection with the embodiments of the invention specifically disclosed herein, it will also be appreciated by those skilled in the art that, depending upon the particular nature of the web being processed, other gripping means well known in the art may also prove suitable i.e., vacuum, etc.

As illustrated in FIGS. 3 – 7, the moisture pervious topsheet 6 is preferably adhered to those portions of the co-terminous moisture-impervious backsheet 5 with which it comes in direct contact by means of any suitable flexible adhesive 7. While the method and apparatus disclosed herein may also be utilized to positively control a web containing discrete stretched strands of elastic adhered at spaced locations along the length of the web, in a preferred embodiment of the present invention the stretched strands of elastic 4 extend continuously along the entire length of the web and are preferably operatively associated with the backsheet 5 of each diaper by means of a second flexible adhesive 7' intermediate the opposed end portions of each hourglass-shaped absorbent pad 3. Those portions of the elastic strands 4 which overlap the absorbent pad 3 and interconnect one diaper to another are preferably unsecured to the diaper web 1. It is therefore preferable that no adhesive be provided in the areas of the diaper through which the unsecured portions of the continuous, stretched elastic strands 4 pass. Thus when the individual diaper segments are severed from the web, as hereinafter described, tension is released on the unsecured portions of the severed elastic strands and the aforementioned unsecured portions assume a relaxed configuration intermediate the topsheet 6 and the absorbent pad 3. Those portions of the severed elastic strands which are secured to the backsheet are, however, maintained in a stretched condition until the transverse fold has been initiated. The hourglass-shaped, semi-rigid absorbent pad 3 is held relatively immobile with respect to the topsheet 6 and backsheet 5 since its lowermost surface is adhered directly to the backsheet 5 by means of the adhesive 7. In addition, it is tightly sandwiched between the topsheet 6 and the backsheet 5 which are adhered to one another about most of the periphery of the pad.

As can be seen in FIGS. 2 and 3, the diapers in the continuous web 1 are joined together in an end-to-end fashion at their waistband portions by means of moisture-impervious backsheet 5, moisture-pervious topsheet 6, the continuous, stretched strands of elastic 4 and the flexible adhesive 7. Because the stretched strands of elastic are preferably adhered only at spaced locations along the length of the web and also because of the discrete shape of the absorbent pads and their relationship to the contoured portions of the topsheet and backsheet, it is extremely important that the diapers contained in the web be maintained in proper register both prior to and during the transverse cutting and transverse folding operations in order to maintain uniform product quality.

Figure 7:
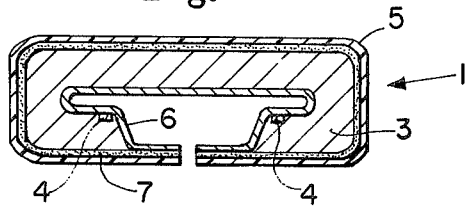
FIG. 7 is an enlarged, simplified cross-sectional view taken along section line 7—7 of FIG. 1, illustrating the condition of the web of disposable diapers after it exits the board folder located at the infeed to the rotary drum.

In a preferred embodiment of applicants' invention, the continuous web 1 of interconnected disposable diapers is fed directly from an assembly line onto a perforated vacuum hold-down belt 10 operating about rolls 9 and 11, as illustrated in FIGS. 1 and 2. Sucton is drawn on the web 1 through the perforated belt 10 by means of a suction box 12 located intermediate rolls 9 and 11 just beneath the innermost surface of the perforated conveyor belt. The purpose of the vacuum hold-down belt is to grip the lowermost surface of the web 1 and thereby provide sufficient resistance to slippage so that tension can be applied to those portions of the web located downstream from the vacuum hold-down belt. Since there is essentially no movement between the lowermost surface of the web 1 and the uppermost surface of the vacuum hold-down belt 10, the web travels at substantially the same velocity as the belt, which for purposes of illustration will be referred to hereinafter as $V_A$. After passing over the vacuum hold-down belt 10, the web 1 is preferably directed about an idler roll 60 and onto the surface of a conventional board folder 13. As is best illustrated in FIGS. 1, 2, 5 and 6, the board folder 13 tapers from an infeed width substantially equal to the maximum width of the diaper in its unfolded condition to a discharge width substantially equal to the overall width of the diaper after C-folding. The lateral edge portions of the diaper web are directed about the board folder 13 by means of cooperation between a pair of infeed guiderails 14, as illustrated in FIGS. 1, 2, and 6, and a slight change in direction of the board folder just prior to the entrance of the C-folded web onto the surface of the rotary drum 15. After leaving the board folder 13, the diaper web 1 has a C-shaped transverse cross-section such as is illustrated in FIG. 7, which is a cross-sectional view of the web taken along section line 7—7 of FIG. 1.

In a preferred embodiment of the present invention, the rotary drum 15 is equipped with four complete diaper handling stations which are equally spaced about its periphery. Thus, with each complete revolution of the drum, four individual diapers are processed, i.e., every 90° of rotation a uniformly cut, transversely folded diaper is discharged from the periphery of the drum. Each diaper handling station is comprised of a pair of leading grippers 16, 23, 30 and 37; a pair of trailing grippers 22, 29, 36 and 43; a reciprocating tucker mechanism 21, 28, 35, and 44; and a cutting anvil 20, 27, 34, and 41. The web 1 may be manually fed onto the surface of the drum so as to initially place it in proper registration for the transverse cutting and folding operations, or a phase variator of a type well known in the art may be provided in the drive system of the drum to initially adjust the position of the web relative to the surface of the drum.

Figure 11:
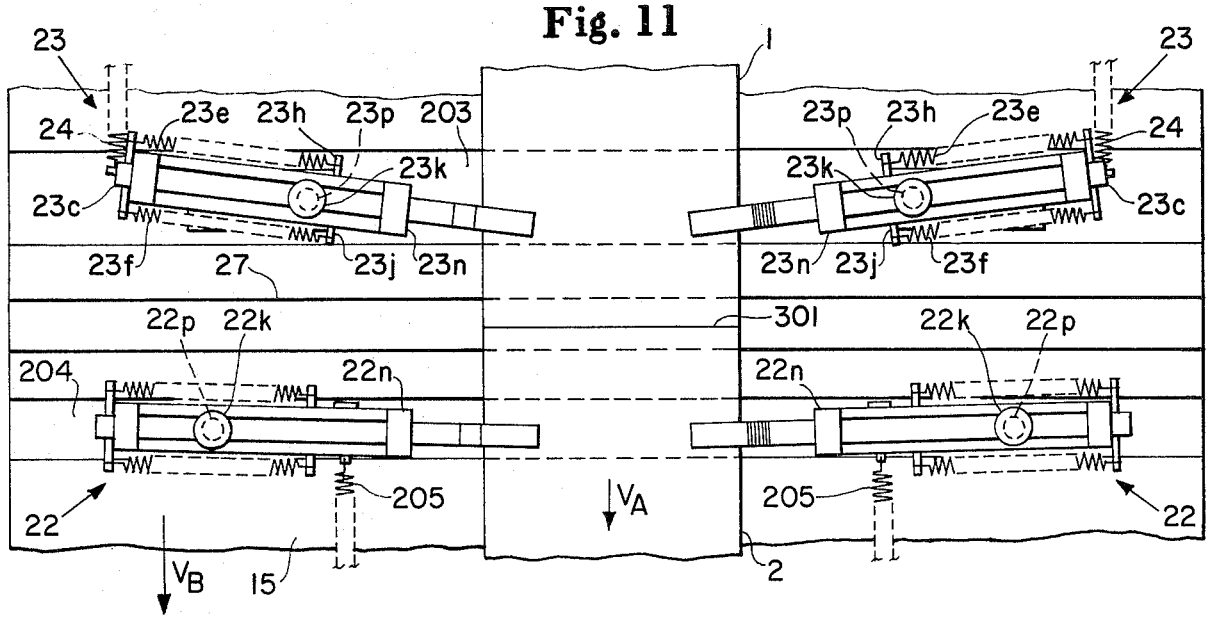
FIG. 11 is an enlarged, simplified view taken along view line 11—11 of FIG. 1, illustrating the relative positioning of a pair of trailing grippers and a pair of leading grippers at the instant an individual diaper is being cut from the web.

As can be seen in FIG. 11 which is typical, the trailing grippers 22 are pivotally mounted about fixed shafts 22p, while the leading grippers 23 are pivotally mounted about fied shafts 23p. Groove 203 in the drum's surface limits the degree of rotation of the leading grippers 23, while groove 204 limits the degree of rotation of the trailing grippers 22. In this regard, it should be noted that the permissible degree of rotation of the leading grippers 23 is considerably greater than the permissible degree of rotation of the trailing grippers 22 due to the greater width of the groove 203 in comparison to the groove 204. The leading grippers 23 are spring loaded in a forward direction, i.e., the direction of web travel, by means of bias springs 24 which are secured to fixed attachment points 25 (FIG. 1) on the surface of the drum 15. The trailing grippers 22 are also spring loaded in a forward direction by means of bias springs 205 which are secured to fixed attachment points 206 (FIG. 1) on the surface of the drum. FIG. 11 depicts the condition of the leading grippers 23 and the trailing grippers 22 at the instant an individual diaper 2 is being cut from the web 1 along line 301. Therefore, both sets of grippers which have just closed on the web are in their home base positions, i.e., trailing grippers 22 are resting against the leading edge of groove 204 while leading grippers 23 are resting against the trailing edge of groove 203, due to the action of the bias springs 205 and 24 which operate in conjunction with fixed pivot shafts 22p and 23p, respectively.

As shown in FIGS. 1 and 11, an individual diaper 2 is cut from the web 1 by means of an anvil 27 mounted on the periphery of the drum 15 and a rotary flex knife 44 having blades 45 and 46 affixed to its periphery. The rotary flex knife 44 is synchronously driven with the rotary drum 15 such that one of its blades makes contact with one of the anvils mounted on the periphery of the drum for every half revolution of the rotary flex knife 44.

FIG. 1 illustrates the condition of the diaper web 1 at the instant an individual diaper 2 is being cut from the web. At this particular instant, leading grippers 16, trailing grippers 22 and leading grippers 23 are in their fully closed position securing both the web 1 and the diaper 2 being cut therefrom to the periphery of the drum 15. The condition of the aforementioned grippers is best illustrated in FIG. 8, which is a cross-sectional view taken along section line 8—8 of FIG. 1.

Figure 8:
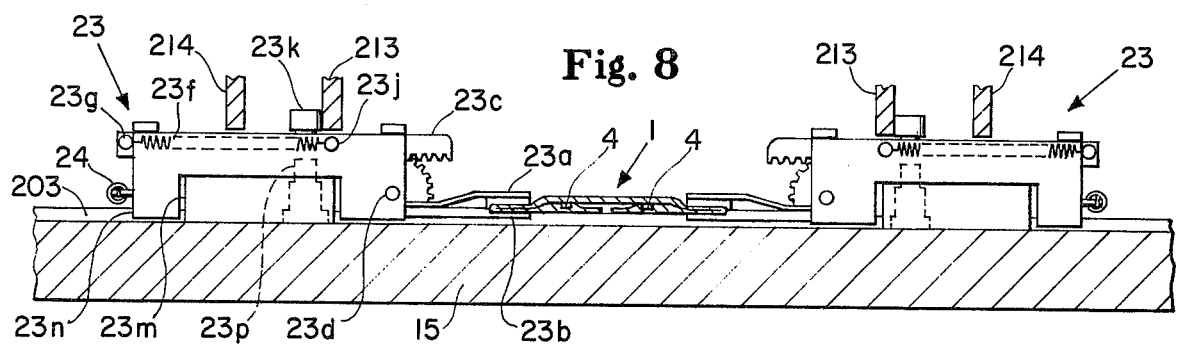
FIG. 8 is an enlarged, simplified cross-sectional view taken along section line 8—8 of FIG. 1, illustrating a pair of gripping elements securing the C-folded diaper web in their fully closed position.
Figure 9:
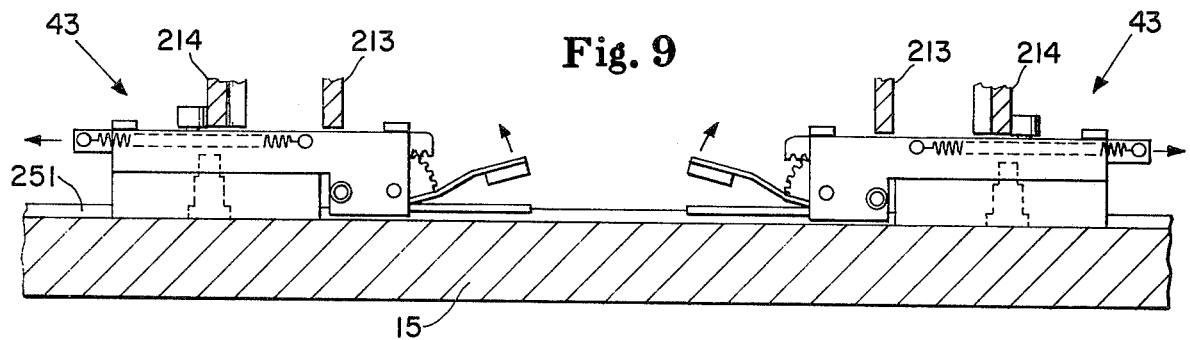
FIG. 9 is an enlarged, simplified illustration taken along section line 9—9 of FIG. 1, illustrating the position of a pair of gripping elements in their partially open position which occurs upon release of the individual diapers into the folding belts.
Figure 10:
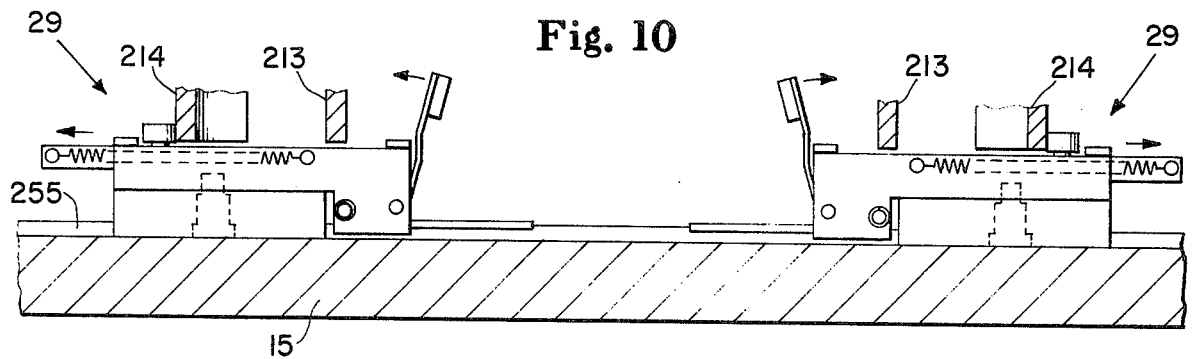
FIG. 10 is an enlarged, simplified illustration taken along section line 10—10 of FIG. 1, illustrating the position of a pair of gripping elements in their fully open position to enable the C-folded diaper web to be fed onto the periphery of the rotary drum.

As can be seen from FIGS. 8 and 11, which are typical, each gripper is comprised of a serrated rack 23c capable of movement in a directin generally parallel to the axis of rotation of the drum 15 in a pivotally mounted housing 23n having a lowermost projection 23b which serves to support the lowermost surface of the web 1. Lateral movement of the rack 23c serves to open and close the uppermost grip finger 23a by means of interaction between the serrations on the rack and the mating surfaces of the gear which is an integral portion of the uppermost gripfinger 23a, thereby causing the uppermost gripfinger to rotate about pivot point 23d. The grippers are spring loaded in a normally closed position by means of bias springs 23e and 23f which are connected to the rack 23c by means of pin 23g and to the pivotally mounted housing 23n by means of pins 23h and 23j. The pivotally mounted housing 23n of the gripper is supported on the surface of the drum 15 by means of fixed pivot shaft 23p and wear block 23m. The rack 23c is caused to move laterally against the bias springs 23e and 23f by means of interaction between cam follower 23k mounted on its uppermost surface and a fixed cam surface 213 shown, for reasons of clarity, only in FIGS. 8-10. A pair of fixed cam surfaces 213 which are concentrically mounted about the periphery of the drum 15 controls the opening and closing of the leading grippers 16, 23, 30 and 37, while a similar pair of fixed cam surfaces 214, shown, for reasons of clarity, only in FIGS. 8-10, controls the opening and closing of the trailing grippers 22, 29, 36 and 43.

The leading grippers and trailing grippers employ the same basic operating principles, and differ from one another only in minor details such as: the location of the fixed shafts about which they are pivoted, i.e., leading grippers 23 are pivoted about fixed shafts 23p while trailing grippers 22 are pivoted about fixed shafts 22p; the location of the bias springs, i.e., leading grippers 23 are spring loaded in a forward direction by means of bias springs 24 while trailing grippers 22 are spring loaded in a forward direction by means of bias springs 205; and the configuration of the pivotally mounted gripper housing, i.e., the leading gripper housing 23n is so designed that its trailing surface is normally held in home base position against the trailing edge of groove 203 in the surface of the drum 15 by means of bias spring 24 while the trailing gripper housing 22n is so designed that its leading surface is normally held in home base position against the leading edge of groove 204 in the surface of the drum by means of bias spring 205.

Figure 12:
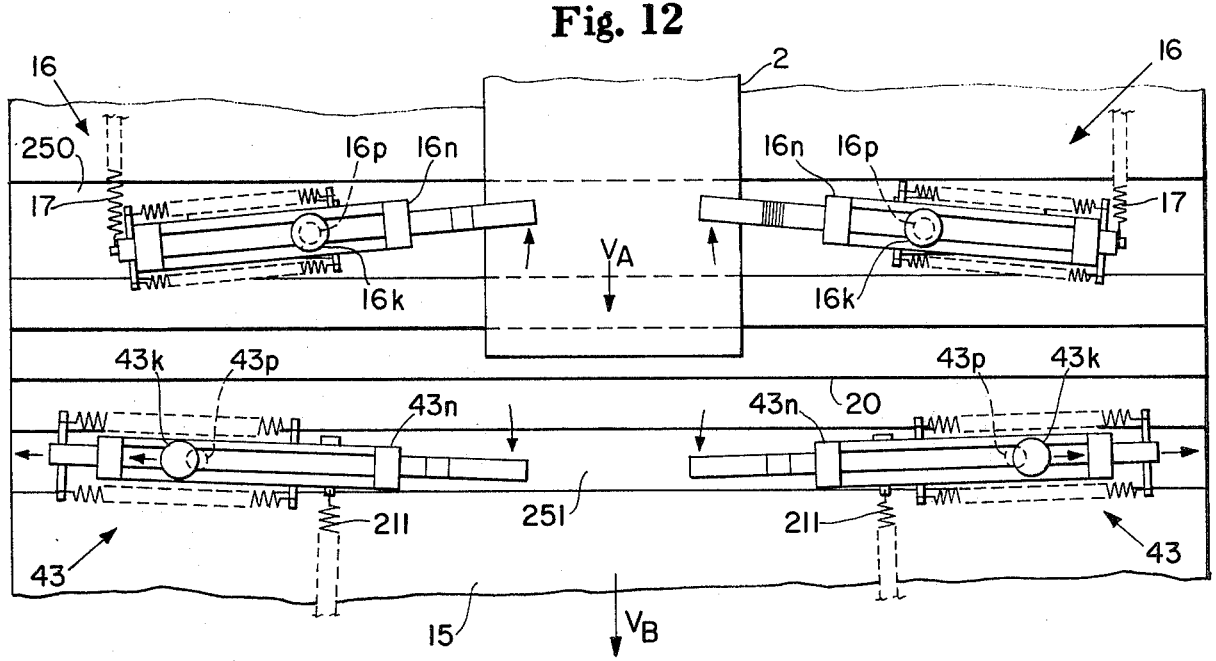
FIG. 12 is an enlarged, simplified view taken along view line 12—12 of FIG. 1, illustrating the relative positioning of a pair of trailing grippers and a pair of leading grippers at the instant the diaper to which the leading grippers are affixed is being cut from the web.

As shown in FIG. 12, the leading grippers 16 are pivotally displaced toward the rear in groove 250 when the web 1 has been advanced a distance equivalent to the length of an individual diaper 2. Thus, the bias springs 17 associated with leading grippers 16 carry the entire tensile load imposed by the resistance of the web 1 while the leading edge of the web is being advanced into position for transverse cutting. The rearward displacement of each pair of leading grippers provides sufficient separation between adjacent diapers to avoid interference between the leading edge of the diaper which has been cut from the web and the trailing edge of the diaper being transversely folded during the transverse folding operation. Sufficient separation is provided by operating the rotary drum 15 at a peripheral velocity $V_B$ which is slightly greater than the infeed velocity of the web $V_A$. Since only one pair of leading grippers secures the web to the drum while the drum is being advanced one station in preparation for the next transverse cut of the web, the difference between the velocity $V_B$ of the periphery of the drum 15 and the velocity $V_A$ of the incoming web 1 causes the web to shift toward the rear relative to the surface of the drum, thereby causing the leading grippers which are securing the leading edge of the web to the surface of the drum to also move rearwardly away from their home base position, as shown in FIG. 11, to the position shown in FIG. 12. This is feasible due to the presence of bias springs, i.e., springs 17, which maintain the web 1 under tension and the continuous elastic strands 4 in a stretched condition while the leading grippers, i.e., grippers 16, are pivoted rearwardly. Just before the individual diaper 2 is cut from the web 1 along line 301, trailing grippers 22 and leading grippers 23 are closed about the web. This prevents loss of control of the individual diaper 2 cut from the web due to a loss of tension in those portions of the stretched strands of elastic which are secured to the web when the transverse cut is completed, and at the same time maintains the leading edge of the diaper web 1 under positive control so that the cycle may be repeated.

As should be apparent from the foregoing description, it is critical that both the individual diapers 2 and the web 1 be maintained under positive control at all times to preserve proper registration of the discrete articles contained therein during both the transverse cutting and the transverse folding operations. Hence, it is critical that the trailing and leading grippers located on opposite sides of the rotary knife 44 be closed prior to completion of the transverse cut. In a preferred embodiment of the present invention, both the trailing and leading grippers are spring loaded in a forward direction. This enables closing of the grippers on the web slightly before the transverse cut is completed, while the web is still moving relative to the surface of the drum, without subjecting the web to damage.

After severance from the web, the individual diapers 2 are folded about their midpoints by means of reciprocating tuckers 21, 28, 35 and 44 which operate in conjunction with an oscillating folding mechanism 47. The oscillating folding mechanism is preferably comprised of a pair of conveyor belts 50 and 53, operating about rolls 48 and 49 and rolls 51 and 52, respectively. The conveyor belts 50 and 53 are fixed relative to each other by means of a pair of side plates 54. The conveyor belts 50 and 53 are preferably operated at a constant velocity $V_C$ which is somewhat greater than the peripheral velocity of the drum $V_B$. The differential between the velocity of the conveyors $V_C$ and the peripheral velocity of the drum $V_B$ is preferably sufficient to avoid any interference between the trailing edge of the diaper being transversely folded and the leading edge of the diaper located immediately behind it on the periphery of the drum during the transverse folding operation.

Figure 13:
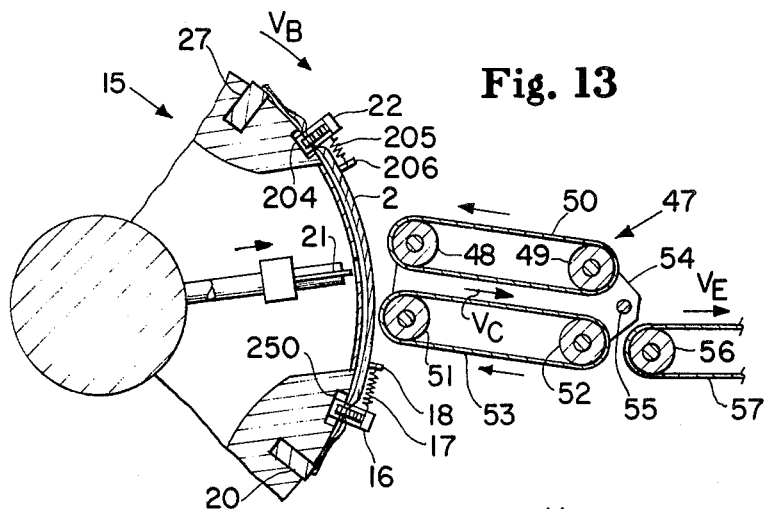
FIG. 13 is a sectional side elevation view of the rotary drum and folding belt mechanism illustrated in FIG. 1 taken at the instant the reciprocating tucking mechanism contained on the periphery of the drum is beginning to oscillate downwardly at approximately the same peripheral velocity as the surface of the drum.
Figure 14:
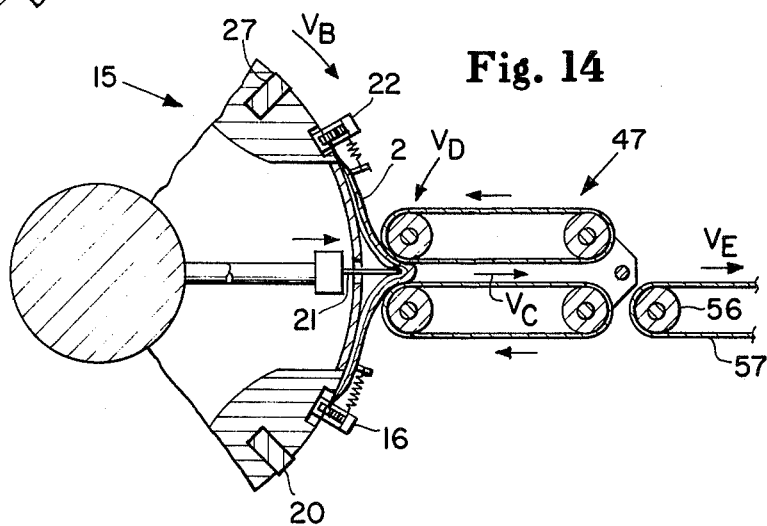
FIG. 14 is a sectional side elevation view of the rotary drum and folding belt mechanism illustrated in FIG. 1 taken at the instant the reciprocating tucking mechanism has reached its fully extended position and the midpoint of the diaper is under the control of the folding belt mechanism, the diaper at this point being free from the grippers which have been partially opened to release the diaper from the surface of the drum.
Figure 15:
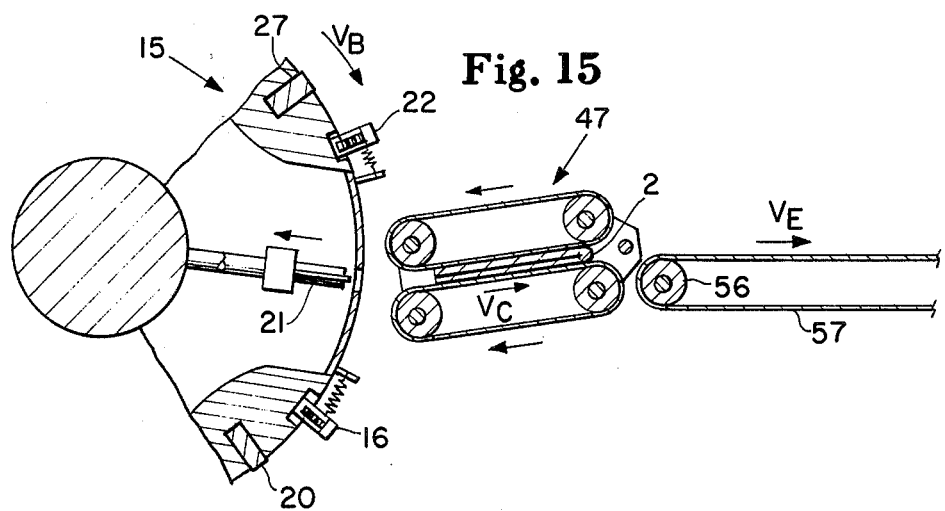
FIG. 15 is a sectional side elevation view of the rotary drum and folding belt mechanism illustrated in FIG. 1 taken at the instant the reciprocating tucking mechanism has reached its fully retracted position and the folding belt mechanism has completed its downward stroke.

The folding mechanism 47 in a preferred embodiment of the present invention is oscillated back and forth about fixed pivot point 55, as is more clearly illustrated in FIGS. 13 – 15. The folding mechanism 47 is driven in synchronization with the rotary drum 15 such that during at least a portion of the time interval illustrated in FIGS. 13 – 15 the peripheral velocity $V_D$ of the folding mechanism 47, as measured at the nip between rolls 48 and 51, is approximately equal to the peripheral velocity $V_B$ of the rotary drum 15. It is during this interval that the reciprocating tucker 21, which is preferably so located on the periphery of the drum 15 that it is aligned with the approximate midpoint of the disposable diaper 2, begins its outward extension. Since the trailing grippers 22 are in their home base position, i.e., the position shown in FIG. 11, with respect to the surface of the drum 15, the location of the transverse fold on the individual diapers 2 may be accurately controlled in this manner.

By the time the rotary drum 15 and the folding mechanism 47 have rotated to the position illustrated in FIG. 14, the reciprocating tucker 21 has reached its fully extended position, thereby inserting the midpoint of the diaper 2 into the nip between conveyor belts 50 and 53 of the folding mechanism 47. The leading grippers 16 and trailing grippers 22 preferably release their grip on the diaper and assume the partially open position illustrated in FIG. 9 at approximately the same instant the diaper 2 comes under the positive control of the folding mechanism 47. As can be seen in FIGS. 14 and 15, the leading grippers 16 and trailing grippers 22, after release of the diaper, return to their home base positions, as illustrated in FIG. 11. It should be noted that at the instant shown in FIG. 14, the reciprocating tucker 21 is beginning its retraction stroke to avoid jamming between the conveyor belts 50 and 53 of the folding mechanism 47 as the rotary drum 15 continues to rotate.

FIG. 15 illustrates the relative positions of the rotary drum and the folding mechanism 47 at a point in time when the reciprocating tucker 21 has been fully retracted and the transversely folded diaper 2 has been completely accepted within the folding mechanism 47.

Oscillating the folding mechanism 47 as shown in FIGS. 13 – 15 to briefly match the peripheral velocity $V_D$ of the folding mechanism 47 and the peripheral velocity $V_B$ of the drum 15 improves the overall speed and reliability of the transverse folding operation due to the fact that the reciprocating tucker mechanism may be operated at a slower cycle speed without necessitating a reduction in the peripheral velocity $V_B$ of the drum. From the foregoing, it should be apparent that the cycle speed of the tucker mechanism must be sufficient to initiate the transverse fold in the manner described above without creating a jam in the folding mechanism 47.

The transversely cut and transversely folded diapers 2 are discharged, ready for packaging, from the folding machanism 47 onto a discharge conveyor 57 which preferably operates about roll 56 at a velocity $V_E$ at least as great as the velocity $V_C$ of the folding belts 50 and 53.

FIG. 23 is a timing chart disclosing a particularly preferred sequence of operation for the elements of one diaper handling station, comprising a pair of leading grippers, i.e., leading grippers 16, a pair of trailing grippers, i.e., trailing grippers 22, and a reciprocating tucker mechanism, i.e., tucker mechanism 21, and the rotary knife 44 during one complete rotation of the drum 15 illustrated in FIG. 1.

Figure 16:
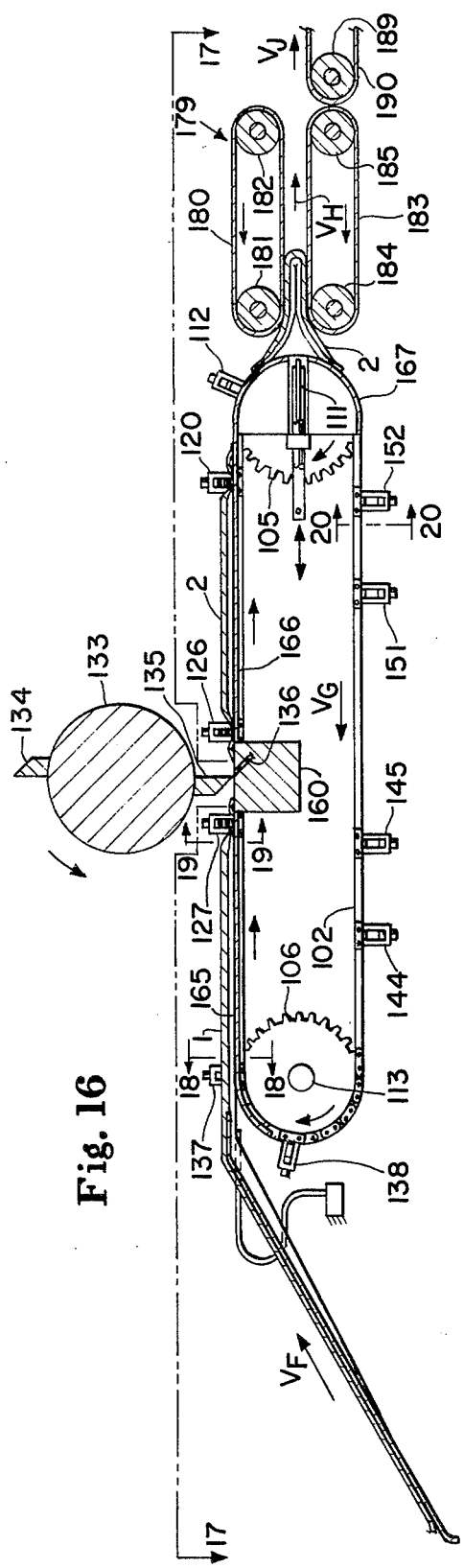
FIG. 16 is a sectional side elevation view of a second embodiment of applicants' invention wherein a plurality of leading and trailing grippers are mounted at spaced locations along the periphery of a plurality of synchronously driven chains, said view being taken in a plane passing through the center line of said web.
Figure 17:
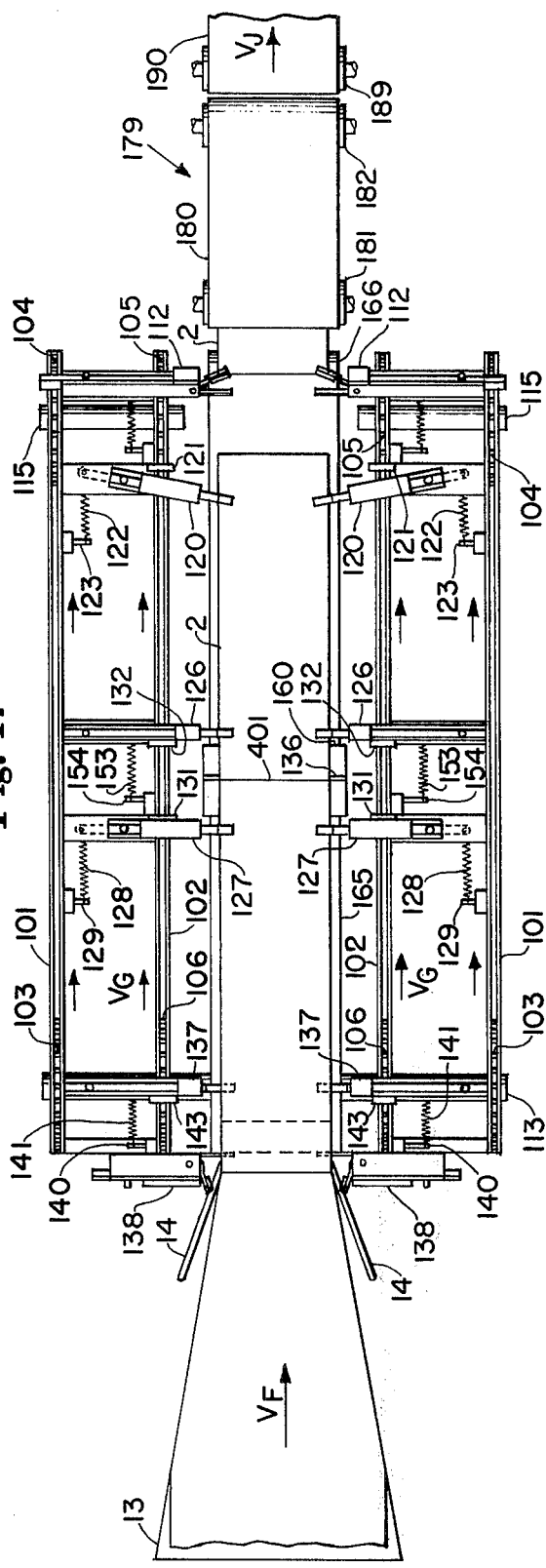
FIG. 17 is a simplified view of the mechanism illustrated in FIG. 16, taken along view line 17—17 of FIG. 16, illustrating the condition of several pairs of leading and trailing grippers at the instant an individual diaper is being cut from the web.

In FIG. 16 is illustrated yet another embodiment of applicant's invention. Although the basic operating principles are similar to those employed on the rotary drum 15 illustrated in FIG. 1, the system illustrated schematically in FIGS. 16 and 17 is comprised of two pairs of chains, i.e., chains 101 and 102, each having a plurality of spring loaded leading and trailing grippers mounted thereto at spaced locations along their length, each pair of chains being operated in synchronization with the other about two pairs of sprockets, i.e., sprockets 103 and 104 and sprockets 105 and 106. As shown in FIG. 17, each pair of infeed sprockets 103 and 106 is secured to a common shaft 113 while each pair of discharge sprockets 104 and 105 is secured to an independent shaft 115 to provide clearance for the reciprocating tucker 111. The incoming diaper web 1 is C-folded by means of a board and guide folder similar to that illustrated in FIG. 1 prior to entry onto the chain folder so that its cross-section is identical to that illustrated in FIG. 7. Stationary web support plates 165, 166 and 167 are provided adjacent the lowermost surface of the web 1 to aid in maintaining the diapers in their C-folded condition and to provide a supporting surface for the individual diapers 2 during the transverse folding operation.

As with the drum folder 15 illustrated in FIG. 1, a pair of leading grippers and a pair of trailing grippers are operatively associated with each diaper 2 contained in the web 1. Each leading gripper, i.e., leading gripper 127, is spring loaded in a forward direction in its home base position against the fixed stop associated with that particular gripper, i.e., stop 131, by means of a bias spring, i.e., spring 128, which is secured to one of the chains by means of a fixed attachment point, i.e., attachment point 129. Each trailing gripper, i.e., trailing gripper 137, is spring loaded in a rearward direction in its home base position against the fixed stop associated with that particular gripper, i.e., stop 143, by means of a bias spring, i.e., spring 141, which is secured to one of the chains by means of a fixed attachment point, i.e., attachment point 140.

The leading and trailing grippers employed on the apparatus illustrated in FIGS. 16 and 17 are basically similar in design to those employed on the apparatus illustrated in FIGS. 1 and 2. It should be noted from FIG. 18 which is typical, however, that the gripper housing 137n is supported on a plate 137r which connects chains 101 and 102. The plate 137r has a boss 137s secured to its lowermost surface and a hole 137t passes through both the plate and the boss. A shaft 137u which is secured to the housing 137n passes through the hole 137t and connects with an arm 137v located on the lowermost surface of the plate. The free end of arm 137v is connected to a bias spring 141 which is secured to one of the chains 102 by means of a fixed attachment point 140. Thus trailing grippers 137 piovt about the hole 137t in plate 137r and boss 137s.

Figure 18:
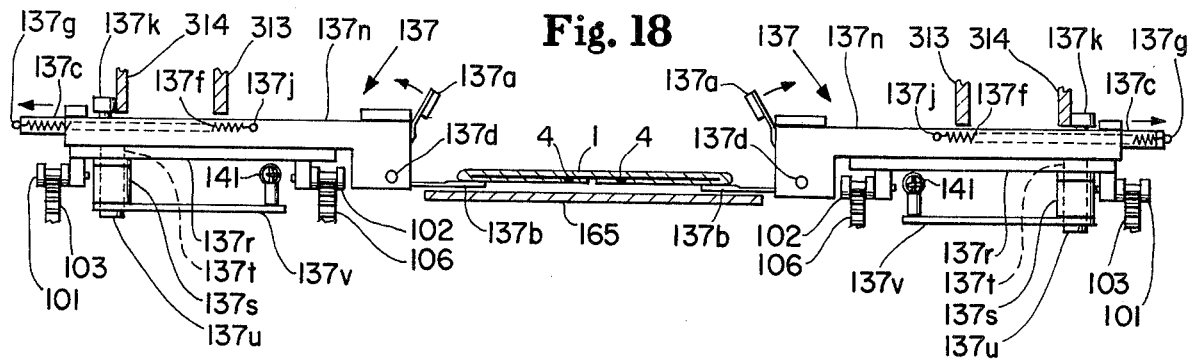
FIG. 18 is an enlarged, simplified cross-sectional view taken along section line 18—18 of FIG. 16, illustrating the condition of a pair of grippers in their fully opened position.
Figure 19:
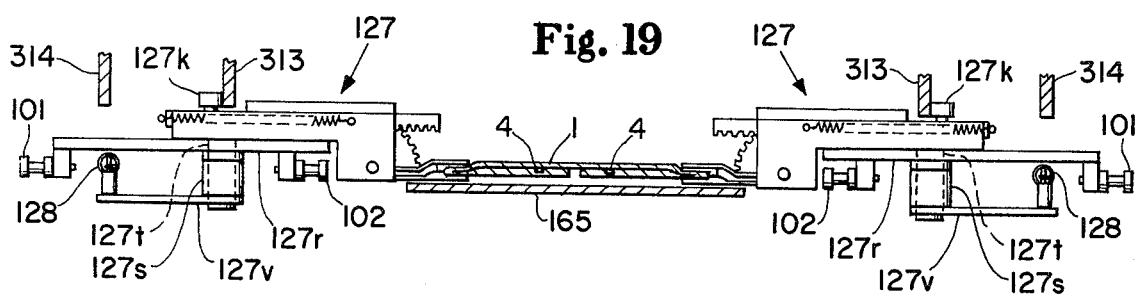
FIG. 19 is an enlarged, simplified cross-sectional view taken along section line 19—19 of FIG. 16, illustrating the condition of a pair of grippers in their fully closed position.

As is apparent from FIGS. 18 and 19, the leading and trailing grippers utilize in the apparatus illustrated in FIGS. 16 and 17 each employ the same basic operating principles, and differ from one another only in minor details such as: the location of their pivot points, i.e., trailing grippers 137 are pivoted about holes 137t in plates 137r and bosses 137s while leading grippers 127 pivot about holes 127t in plates 127r and bosses 127s; the location of the bias springs, i.e., trailing grippers 137 are spring loaded in a rearward direction by means of bias springs 141 while leading grippers 127 are spring loaded in a forward direction by means of bias springs 128; and the configuration of the pivotally mounted gripper housing, i.e., trailing gripper housing 137n has a greater overall length than leading gripper housing 127n to accommodate the difference in the location of their pivot points.

FIG. 16 depicts the condition of the web 1 the instant a disposable diaper 2 is being cut from the web along line 401 by means of cooperation between the rotary cylinder 133 having blades 134 and 135 mounted on its periphery and a flex knife 136 mounted in stationary support 160. Since the velocity of the chains $V_G$ is slightly greater than the incoming velocity of the web $V_F$, each leading pair of grippers is displaced rearwardly as the diaper web is advanced a distance equivalent to the overall length of one diaper for the next cut.

Figure 20:
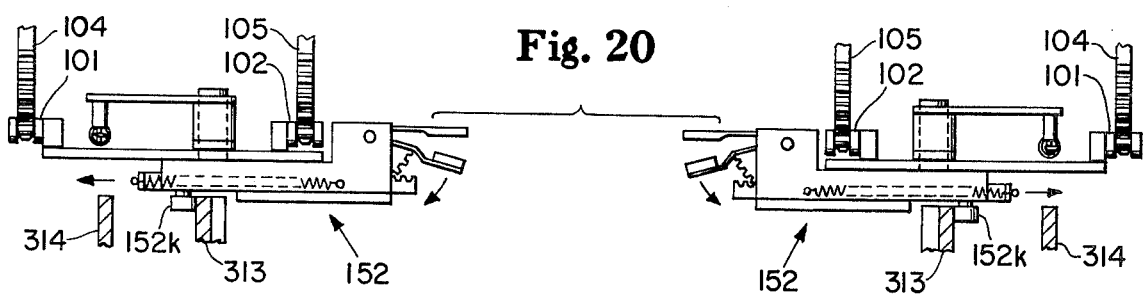
FIG. 20 is an enlarged, simplified cross-sectional view taken along section line 20—20 of FIG. 16, illustrating the condition of a pair of grippers in their partially opened condition.
Figure 21:
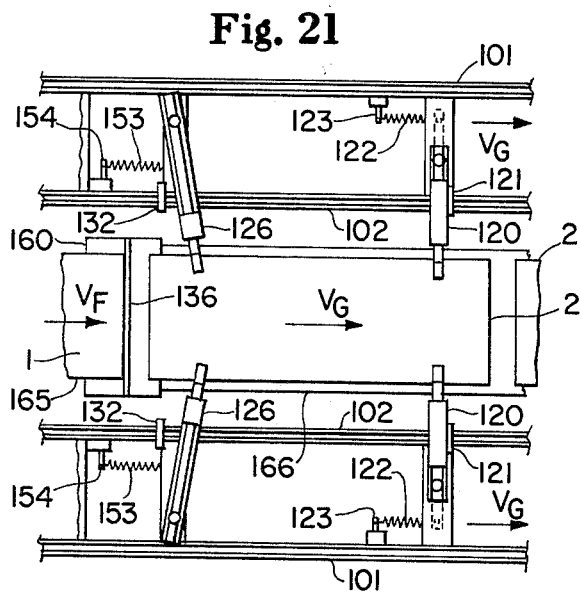
FIG. 21 is a simplified partial plan view of the apparatus illustrated in FIG. 17, illustrating the condition of a pair of leading and trailing grippers after completion of the transverse cut.

As is apparent from FIGS. 16 and 17, leading grippers 120 which secure the leading edge of the diaper web 1 prior to completion of the transverse cutting operation have pivoted rearwardly, thus placing bias springs 122 under stress. Just prior to completion of the transverse cut along line 401, trailing grippers 126 and leading grippers 127 which are located on opposite sides of the knife blades 135 and 136 assume the closed position illustrated in FIG. 19 due to the interaction of the cam followers associated with each gripper, i.e., cam followers 127k and 126k, and the fixed cam surfaces 313 and 314 which are mounted about the periphery of the chains, said cam surfaces being shown, for reasons of clarity, only in FIGS. 18 – 20. This is necessary to avoid losing control of either the leading edge of the diaper web 1 or the individual diaper 2 severed therefrom after the transverse cut has been effected. It should be noted that since the trailing grippers cannot be rearwardly displaced from their home base positions in the apparatus illustrated in FIGS. 16 and 17, it is critical that the closing of the trailing grippers be timed to coincide as closely as is feasible with the completion of the transverse cut to avoid web damage. After the transverse cut has been completed, the individual diaper 2 cut from the web is maintained under tension to keep the secured portions of the severed strands of elastic 4 in a stretched condition, but the severed diaper is immediately forwardly displaced, as illustrated in FIG. 21, due to the fact that the bias springs associated with each leading pair of grippers, i.e., springs 122, have a greater spring rate than the bias springs associated with each trailing pair of grippers, i.e., springs 153. Thus, the individual diapers 2 cut from the web 1 are maintained under positive control and are accurately positioned for transverse folding by means of a leading pair of grippers resting against the fixed stops associated with their home base positions and a trailing pair of grippers which are forwardly displaced away from their home base positions, as illustrated in FIG. 21.

Figure 22:
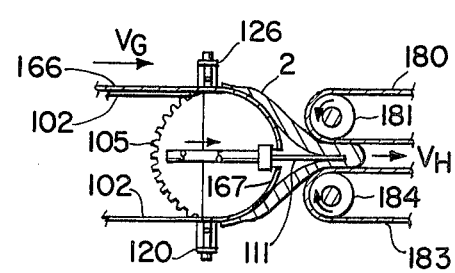
FIG. 22 is a partial sectional side elevation view of the apparatus illustrated in FIG. 16, illustrating the condition of the reciprocating tucking mechanism in its fully extended position.

A reciprocating tucker mechanism 111 located intermediate the two pairs of discharge sprockets 104 and 105 of the apparatus preferably contacts the individual diapers 2 at their midpoints and inserts them into a folding mechanism 179, as shown in FIG. 22.

In a preferred embodiment, the folding mechanism 179 is comprised of a pair of conveyor belts 180 and 183 which operate about rolls 181 and 182 and rolls 184 and 185, respectively. Each conveyor belt is fixed relative to the other. The reciprocating tucker 111 inserts the midpoint of each diaper into the nip formed between the conveyor belts 180 and 183. At approximately the same instant the diaper comes under the positive control of the conveyor belts, the leading and trailing grippers associated with the diaper being transversely folded, i.e., leading grippers 120 and trailing grippers 126, are caused to assume the partially open position illustrated in FIG. 20 and the reciprocating tucker 111 is retracted. Each pair of leading and trailing grippers is thereafter caused to assume the fully open position illustrated in FIG. 18 prior to reaching the C-folded diaper web 1 at the infeed end of the apparatus to permit the diaper web to enter the grippers without interference.

The stationary conveyor belts 180 and 183 are preferably operated at a velocity $V_H$ which is sufficiently greater than the velocity $V_G$ of the chains to avoid interference between the trailing edge of the diaper being transversely folded and the leading edge of the diaper immediately following. In this regard, it should be noted that it is critical that the individual diapers 2 be separated from one another by a minimum predetermined distance, the exact distance being a function of the relationship between the velocity $V_H$ of the conveyor belts 180 and 183 of the folding mechanism 179, the velocity $V_G$ of the two pairs of chains 101 and 102, and the cycle speed of the reciprocating tucker 111. It should further be noted that the cycle speed of the reciprocating tucker 111 is directly related to the peripheral velocity $V_G$ of the two pairs of chains 101 and 102 with the apparatus illustrated in FIGS. 16 and 17 due to a lack of dwell time between the tucker and the folding mechanism. The transversely cut and folded diapers 2 are discharged, ready for packaging, from the folding mechanism 179 onto a discharge conveyor 190 which preferably operates about roll 189 at a velocity $V_J$ at least as great as the velocity $V_H$ of the conveyor belts 180 and 183.

FIG. 24 is a timing chart for the five station apparatus illustrated in FIGS. 16 and 17, and shows a particularly preferred sequence of operation between a pair of leading grippers, i.e., leading grippers 120, a pair of trailing grippers, i.e., trailing grippers 126, the reciprocating tucking mechanism 111, and the rotary knife 133. As will be apparent to those skilled in the art, the exact timing sequence may be varied somewhat from that shown, so long as both the diaper web and the individual diapers cut from the web are maintained in register with one another and under positive control throughout the operations shown and described herein.

Thus, it is apparent that there has been provided, in accordance with the present invention, method and apparatus for positively controlling a web of interconnected, elasticized articles, and for performing a series of operations in accurate register not only on said web, but also on the discrete articles cut therefrom. It should be noted, however, that while the invention has been described in conjunction with specific preferred embodiments thereof, it is evident that many alternatives, modifications and variations will be apparent to those skilled in the art in light of the foregoing description. Accordingly, it is intended to embrace all such alternatives, modifications, and variations that fall within the spirit and broad scope of the appended claims.

What is claimed is:

1. A positive control method for transversely cutting discrete articles, each article having at least one stretched elastic member secured thereto in a direction generally parallel to its length, from an interconnected continuously traveling web of said discrete articles and for transversely folding the severed articles about a predetermined point along their length, said method comprising the steps of successively:
   a. grasping the leading portion of a first such article contained in said web at a first predetermined point along its length;
   b. advancing said web a predetermined distance equivalent to the length of one of said articles while maintaining said web and the stretched elastic member secured thereto in tension sufficient to prevent puckering of said web;
   c. grasping the trailing portion of said first article at a second predetermined point along its length prior to severance of said first article from said web;
   d. transversely severing said first article from said web at a third predetermined point intermediate said first article and the adjacent article contained in said web while maintaining said first article, said web and the stretched elastic members secured to said article and said web in tension sufficient to prevent puckering of said article and said web; and
   e. transversely folding said first article about a fourth predetermined point along its length by maintaining said article and the stretched elastic member secured thereto in tension sufficient to prevent puckering of said article until the transverse fold has been initiated.

2. The method of claim 1, wherein said web is comprised of a plurality of discrete disposable diapers interconnected one to another at their waistband portions, each of said disposable diapers having stretched elastic leg bands oriented in a direction generally parallel to the direction of web travel secured thereto, and wherein said diapers are transversely folded about their midpoints after severance from said web.

3. The method of claim 2, including the step of folding the lateral edge portions of said web inwardly into superposition with the central portion of said web to form a C-shaped transverse cross-section prior to severing said diapers from said web.

4. A positive control method for transversely cutting discrete articles, each article having at least one stretched elastic member secured thereto in a direction generally parallel to its length from a continuously traveling web containing said discrete articles in spaced longitudinal relation therealong and for transversely folding the severed articles about a predetermined point along their length, said method comprising the steps of successively:
   a. grasping the leading portion of a first such article contained in said web at a first predetermined point along its length;
   b. advancing said web a predetermined distance equivalent to the length of one of said articles while maintaining said web and the stretched elastic member secured thereto in tension sufficient to prevent puckering of said web;
   c. grasping the trailing portion of said first article contained in said web at a second predetermined point along its length prior to severance of said first article from said web;
   d. grasping the leading portion of the article adjacent said first article at a point corresponding to said first predetermined point at which said first article was grasped to maintain control of said web after severance of said first article therefrom;
   e. transversely severing said first article from said web at a third predetermined point located intermediate said first article and said adjacent article contained in said web while maintaining said first article, said web and the stretched elastic members secured to said article and said web in tension sufficient to prevent puckering of said article and said web; and f. transversely folding said first article about a fourth predetermined point along its length by maintaining said article and the stretched elastic member secured thereto in tension sufficient to prevent puckering of said article until the transverse fold has been initiated.

5. The method of claim 4, wherein said web is comprised of a plurality of disposable diapers interconnected one to another at their waistband portions, each of said disposable diapers having stretched elastic leg bands oriented in a direction generally parallel to the direction of web travel secured thereto, and wherein said diapers are transversely folded about their midpoints after severance from said web.

6. The method of claim 5, including the step of folding the lateral edge portions of said web inwardly into superposition with the central portion of said web to form a C-shaped transverse cross-section prior to severing said diapers from said web.

7. The method of claim 4, wherein the locations of said transverse cut is maintained in accurate register intermediate adjacent articles contained in said web by applying a uniform degree of tension to said web at the instant said articles are severed therefrom.

8. The method of claim 7, wherein the degree of tension applied to said web is increased as said web is advanced into position for transverse cutting, said degree of tension reaching a uniform predetermined level at the instant said articles are severed from said web.

9. The method of claim 4, wherein the location of said transverse fold is maintained in accurate register at a predetermined point along the length of said articles by applying a uniform degree of tension to each of said articles at the instant said transverse fold is initiated.

10. The method of claim 9, wherein said diapers are transversely folded about their midpoints by introducing the midpoints of said diapers into the nip formed between a pair of conveyor belts.

11. A positive control apparatus for successively transversely cutting articles having at least one stretched elastic member secured thereto in a direction generally parallel to their length from a continuously traveling web containing said articles in spaced longitudinal relation therealong and for transversely folding the severed articles about a predetermined point along their length, said apparatus comprising:

a. first gripping means for grasping the leading portion of a first such article contained in said web at a first predetermined point along its length;

b. drive means for advancing said web a predetermined distance equivalent to the length of one of said articles while maintaining said web and the stretched elastic member secured thereto in tension sufficient to prevent puckering of said web;

c. second gripping means for grasping the trailing portion of said first article at a second predetermined point along its length prior to severance of said first article from said web;

d. cutting means for transversely severing said first article from said web at a third predetermined point intermediate said first article and the adjacent article contained in said web while maintaining said first article, said web and the stretched elastic members secured thereto in tension sufficient to prevent puckering of said article and said web; and e. means for transversely folding said first article about a fourth predetermined point along its length, said means including means for maintaining said article and the stretched elastic member secured thereto in tension sufficient to prevent puckering of said article until the transverse fold has been initiated.

12. The apparatus of claim 11, wherein said means for transversely folding said articles about said fourth predetermined point along their length after severance from said web is comprised of a pair of opposed conveyor belts and a reciprocating tucker blade which inserts said articles into the nip formed between said conveyor belts at said predetermined points along their length.

13. The apparatus of claim 12, including means for folding the lateral edge portions of said web inwardly into superposition with the central portion of said web to form a C-shaped, transverse cross-section prior to transversely severing said articles from said web.

14. A positive control apparatus for successively transversely cutting articles having at least one stretched elastic member secured thereto in a direction generally parallel to their length from a continuously traveling web containing said articles in spaced longitudinal relation therealong and for transversely folding the severed articles about a predetermined point along their length, said apparatus comprising:

a. means for grasping the leading portion of a first such article contained in said web at a first predetermined point along its length;

b. drive means for advancing said web a predetermined distance equivalent to the length of one of said articles while maintaining said web and the stretched elastic member secured thereto in tension sufficient to prevent puckering of said web;

c. means for grasping the trailing portion of said first article at a second predetermined point along its length prior to severance of said first article from said web;

d. means for grasping the leading portion of the article adjacent said first article at a point corresponding to said first predetermined point at which said first article was grasped;

e. cutting means for transversely severing said first article from said web at a third predetermined point located intermediate said first article and said adjacent article while maintaining both said first article and said web under tension sufficient to prevent puckering thereof; and f. means for transversely folding said first article about a fourth predetermined point along its length, said means including means for maintaining said article and the stretched elastic member secured thereto under a uniform degree of tension sufficient to prevent puckering of said article until the transverse fold has been initiated.

15. The apparatus of claim 14, wherein said means for grasping the leading portion of each article contained in said web apply a uniform degree of tension to said web at the instant said articles are severed therefrom, thereby maintaining the location of the transverse cut in accurate register intermediate adjacent articles contained in said web.

16. The apparatus of claim 14, wherein said means for grasping the leading portion of each article contained in said web and said means for grasping the trailing portion of each article contained in said web apply a uniform degree of tension to each of said articles at the instant said transverse fold is initiated thereby maintaining the location of said transverse fold in accurate register at a predetermined point along the length of said articles.

17. The apparatus of claim 14, including means for folding the lateral edge portions of said web inwardly into superposition with the central portion of said web to form a C-shaped transverse cross-section prior to transversely severing said articles from said web.

18. The apparatus of claim 14, wherein said means for grasping the leading portion of each article contained in said web and said means for grasping the trailing portion of each article contained in said web are each comprised of a pair of pivotally-mounted grippers capable of opening and closing about said web to secure said web along its lateral edge portions, said grippers being resiliently biased in the direction of web travel about their pivot points.

19. The apparatus of claim 14, wherein said means for transversely cutting said web is comprised of a rotary knife and an anvil.

20. The apparatus of claim 14, wherein said means for transversely folding said articles is comprised of a pair of synchronously driven, opposed conveyor belts having a fixed gap spacing therebetween and a reciprocating tucker blade which contacts said articles at said fourth predetermined point along their length while said articles are maintained under a uniform degree of tension between said means for grasping the leading portion of said articles and said means for grasping the trailing portion of said articles and thereafter inserts said articles into the nip formed between said conveyor belts about said predetermined points along their length.

21. The apparatus of claim 20, wherein a plurality of said means for grasping said articles are provided at spaced locations about the periphery of a rotating drum and a reciprocating tucker blade is provided on the periphery of said drum intermediate each of said means for grasping the leading portion of said articles and said means for grasping the trailing portion of said articles, said apparatus including means for matching the peripheral velocity of said drum with the peripheral velocity of the nip formed between said conveyor belts while said articles are being inserted therebetween.

22. The apparatus of claim 21, including means for rotating said drum at a peripheral velocity which exceeds the incoming tangential velocity of said web, thereby maintaining said web and the stretched elastic member secured thereto in tension sufficient to prevent puckering of said web.

* * * * *

UNITED STATES PATENT AND TRADEMARK OFFICE
CERTIFICATE OF CORRECTION

PATENT NO. : 4,022,456
DATED : May 10, 1977
INVENTOR(S) : Leonard C. Hooper and Gerald M. Weber It is certified that error appears in the above-identified patent and that said Letters Patent are hereby corrected as shown below:

Column 3, line 7, delete "tie" and insert therefor -- time --.

Column 3, line 24, delete "forementioned" and insert therefor -- aforementioned --.

Column 4, lines 24 and 25, after "beginning" insert -- its outward advance and the folding belt mechanism is beginning --.

Column 5, line 58, delete "moisture pervious" and insert therefor -- moisture-pervious --.

Column 7, line 31, delete "fied" and insert therefor -- fixed --.

Column 8, line 9, delete "directin" and insert therefor -- direction --.

UNITED STATES PATENT AND TRADEMARK OFFICE
CERTIFICATE OF CORRECTION

PATENT NO. : 4,022,456
DATED : May 10, 1977
INVENTOR(S) : Leonard C. Hooper and Gerald M. Weber It is certified that error appears in the above-identified patent and that said Letters Patent are hereby corrected as shown below:

Column 11, line 55, delete "piovt" and insert therefor -- pivot --.

Column 15, Claim 7, line 25, delete "locations" and insert therefor -- location --.

Signed and Sealed this

Second Day of May 1978

[SEAL]

Attest:

RUTH C. MASON
Attesting Officer

LUTRELLE F. PARKER
Acting Commissioner of Patents and Trademarks